US008594757B2

(12) United States Patent
Boppart et al.

(10) Patent No.: US 8,594,757 B2
(45) Date of Patent: Nov. 26, 2013

(54) APPARATUS FOR BIOMEDICAL IMAGING

(75) Inventors: Stephen A. Boppart, Champaign, IL (US); Woonggyu Jung, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 135 days.

(21) Appl. No.: 12/946,805

(22) Filed: Nov. 15, 2010

(65) Prior Publication Data

US 2011/0130652 A1 Jun. 2, 2011

Related U.S. Application Data

(60) Provisional application No. 61/262,429, filed on Nov. 18, 2009.

(51) Int. Cl.
*A61B 5/00* (2006.01)

(52) U.S. Cl.
USPC ........... 600/310; 600/407; 600/473; 600/476; 600/160

(58) Field of Classification Search
USPC .......................... 600/407, 473, 476, 160, 310
See application file for complete search history.

(56) References Cited

U.S. PATENT DOCUMENTS 6,485,413 B1 * 11/2002 Boppart et al. ............... 600/160
2009/0048520 A1 * 2/2009 Marteau et al. ............... 600/459

OTHER PUBLICATIONS

Aguirre et al., "Two-Axis MEMS Scanning Catheter for Ultrahigh Resolution Three-Dimensional and En Face Imaging", Department of Electrical Engineering and Computer Science and Research Laboratory of Electronics Massachusetts Institute of Technology, Cambridge MA, USA—Revised Feb. 12, 2007; accepted Feb. 14, 2007; OSA Mar. 5, 2007, vol. 15, No. 5 / Optics Express; pp. 2445-2453.
Boppart, "Optical Coherence Tomography: Technology and Applications for Neuroimaging", Department of Electrical and Computer Engineering, Bioengineering Program, and Beckman Institute for Advance Science and Technology, College of Medicine, University of Illinois at Urbana-Champaign, Urbana, IL, USA—accepted Nov. 24, 2002; pp. 529-541.
Gerth et al., "High-Resolution Retinal Imaging in Young ChildrenUsing a Handheld Scanner and Fourier-Domain Optical Coherence Tomography", Journal of AAPOS, vol. 13, No. 1, Feb. 2009; pp. 72-74e1.
Grieve et al., "In Vivo Anterior Segment Imaging in the Rat Eye With High Speed White Light Full-Field Optical Coherence Tomography", Optical Society of America; revised May 20, 2005; revised Aug. 1, 2005; OSA Aug. 8, 2005, vol. 13, No. 16 / Optics Express; pp. 6286-6295.
Su et al., "In vivo Three-Dimensional Microelectromechanical Endoscopic Swept Source Optical Coherence Tomography", Department of Biomedical Engineering, University of California, Irvine, CA, USA—Revised Jul. 23, 2007; accepted Jul. 26, 2007; OSA Aug. 6, 2007, vol. 15, No. 16 / Optics Express; pp. 10390-10396.

(Continued)

*Primary Examiner* — Unsu Jung
*Assistant Examiner* — Joel Lamprecht
(74) *Attorney, Agent, or Firm* — Guntin & Gust, PLC; Andrew Gust

(57) ABSTRACT

A system that incorporates teachings of the present disclosure may include, for example, a method involving capturing spectral interference from an optical coherence tomography imaging probe comprising a micro-electro-mechanical system (MEMS) scanning mirror, and a partial reflector for supplying images to an image sensor. Additional embodiments are disclosed.

27 Claims, 19 Drawing Sheets

(56) References Cited

OTHER PUBLICATIONS

Tran et al., "In Vivo Endoscopic Optical Coherence Tomography by Use of a Rotational Microelectromechanical System Probe", Department of Biomedical Engineering and Beckman Laser Institute, University of California, Irvine, CA, USA—Optical Society of America, Optics Letters vol. 29, No. 11, Jun. 1, 2004; pp. 1236-1238.

Vabre et al., "Thermal-Light Full-Field Optical Coherence Tomography", Laboratoire d'Optique Physique, Ecole Superieure de Physique et de Chimie Industrielles, Centre National de la Recherche Scientifique, Unite Prope de Recherche, Paris, France; Optics Letters vol. 27, No. 7, Apr. 1, 2002; pp. 530-532.

Wang et al., "In Vivo Bladder Imaging with Microelectromechanical-Systems-Based Endoscopic Spectral Domain Optical Coherence Tomography", Journal of Biomedical Optics vol. 12(3), (May/Jun. 2007); pp. 034009-1 to 034009-8.

\* cited by examiner

| Companies (country) | Specification |
|---|---|
| Optovue (USA) | Wavelength: 810 ~ 840 nm |
| Topcon (Japan) | Exposure Power at Cornea: 650 ~ 750 µW |
| Carl Zeiss Meditec (Germany) | Scanning Speed: 18,000 ~ 52,000 A-scan/second<br>Frame Rate: 8, 16, 32 frames/second |
| OPKO/OTI (USA) | Depth Resolution: (in tissue): 3.0 ~ 10 µm |
| Optopol (Poland) | Transverse Resolution: 12 ~ 20 µm |
| Bioptigen (USA) | Imaging Depth: 2 ~ 2.3 mm |
| Heidelberg Engineering (Germany) | Field of View: 2 mm ~ 12 mm (Up to 30° angle) |

*Prior Art*

FIG. 1

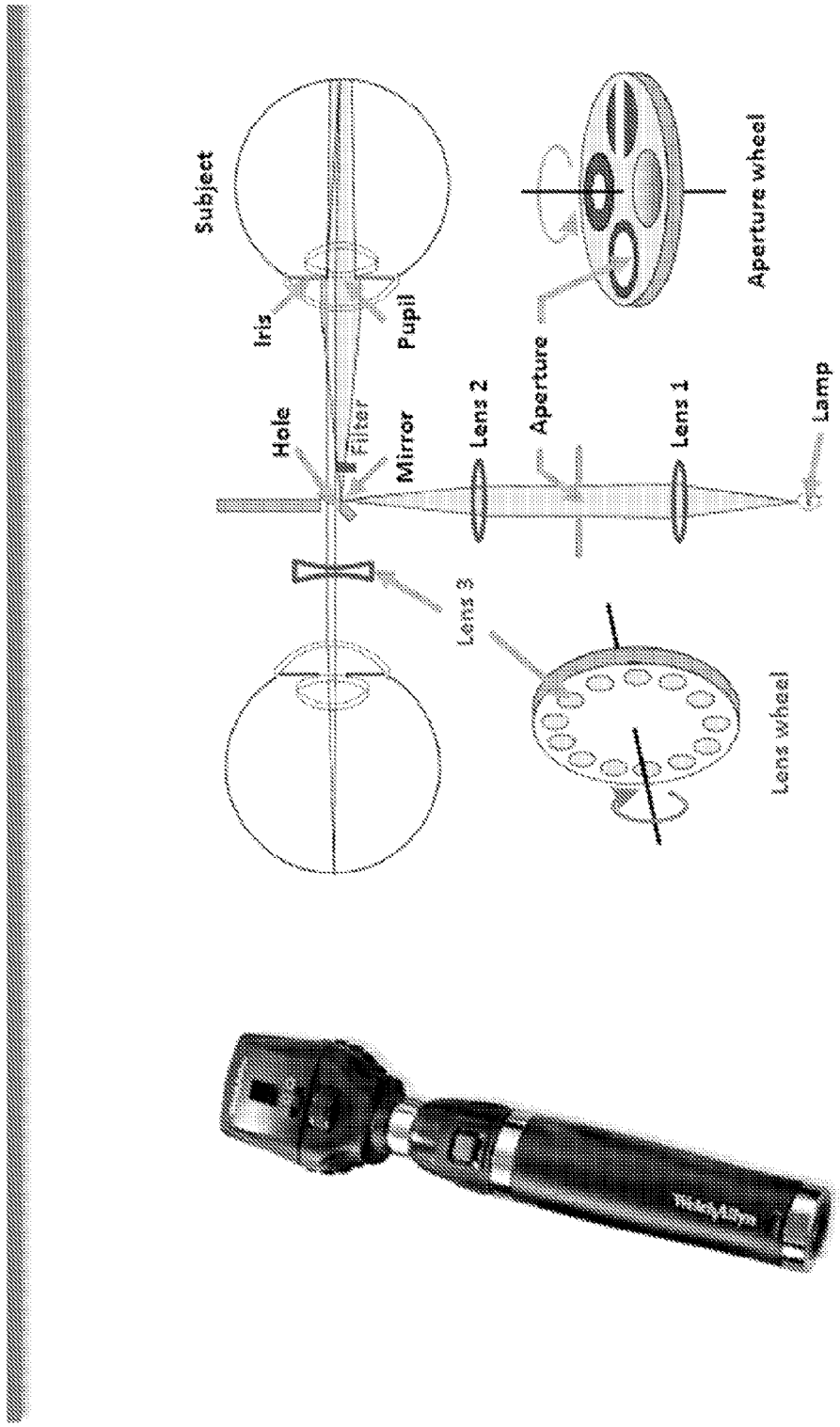
*Prior Art*
FIG. 2B
*Prior Art*
FIG. 2A

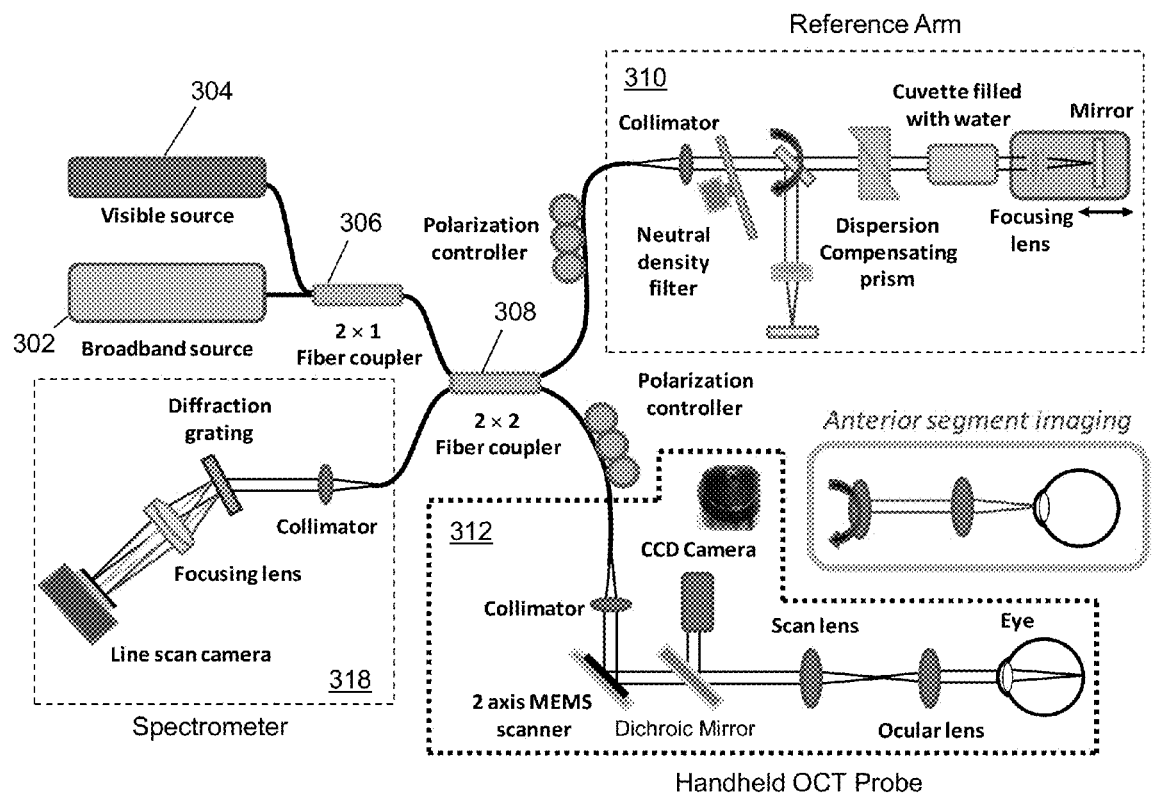
FIG. 3

2 Axes MEMS Scanner
- Four Quadrant MEMS Scanner
  (Electrostatic Comb Driven Actuator)
- Mirror size: 2.2 mm, 3.2 mm,    Die Size: 3.3 mm × 2.6 mm
  – Mirrors have 1.5 to 2 μm thickness with 20 μm trusses.
- Resonance frequency: 1 kHz in both axis (@2.2 mm diameter)
- Angle: up to 20°
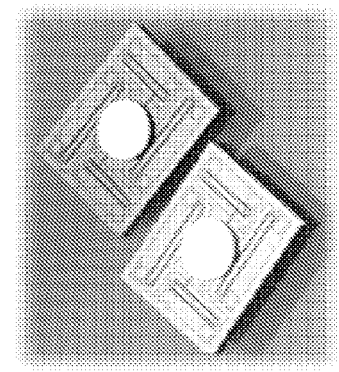
FIG. 4A
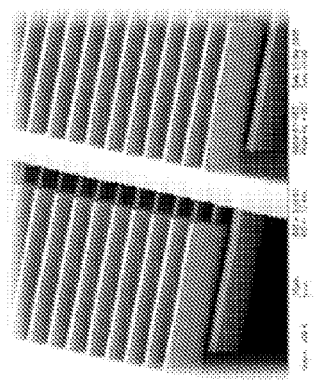
FIG. 4B
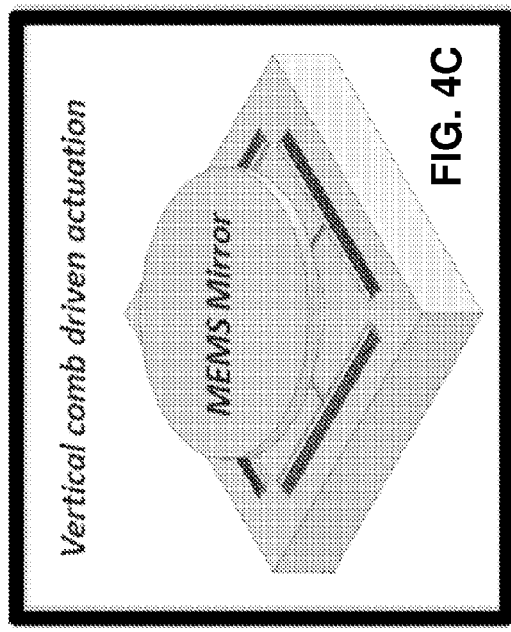
FIG. 4C

2 Axes MEMS Scanner
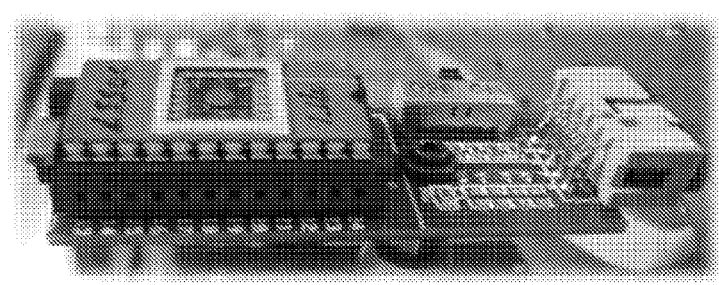
FIG. 5A  FIG. 5B  FIG. 5C  FIG. 5D  FIG. 5E

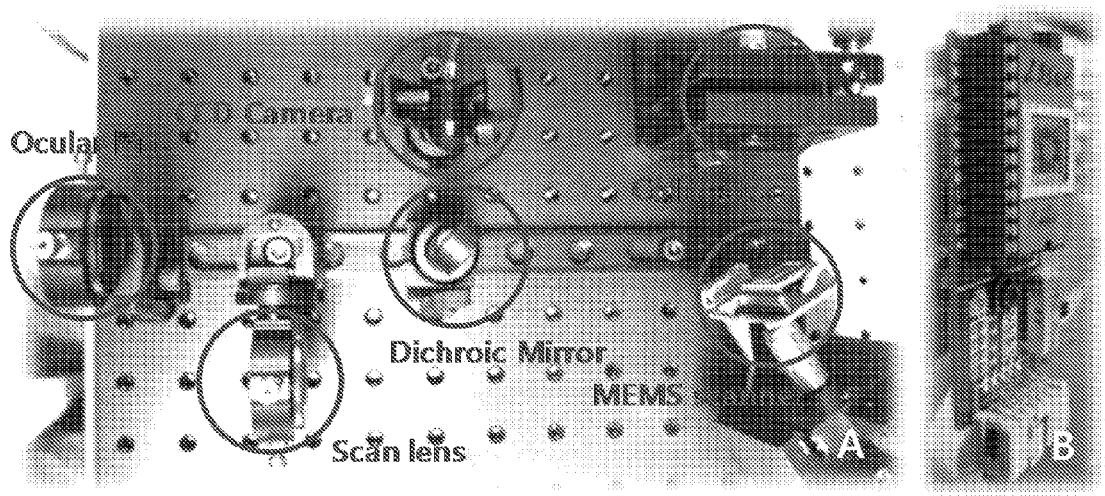
FIG. 6A  FIG. 6B

 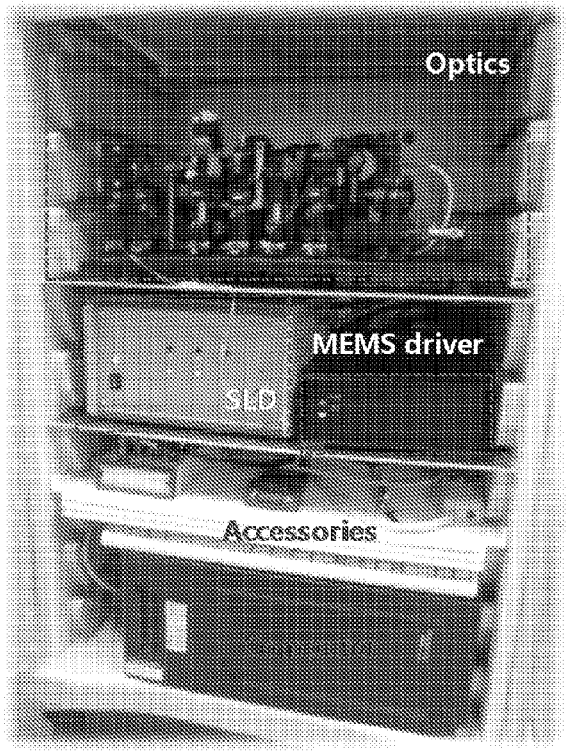
FIG. 7A              FIG. 7B

- *Packaging of Handheld OCT Probe*
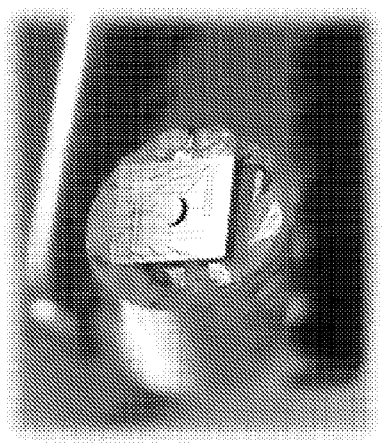
FIG. 8A
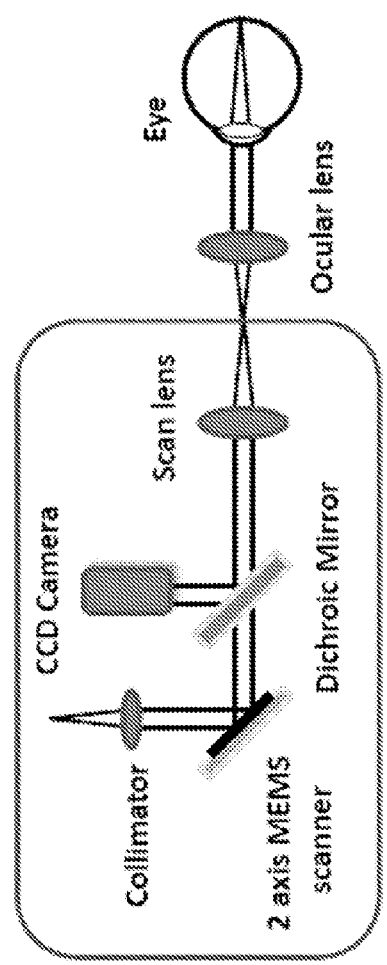
FIG. 8B
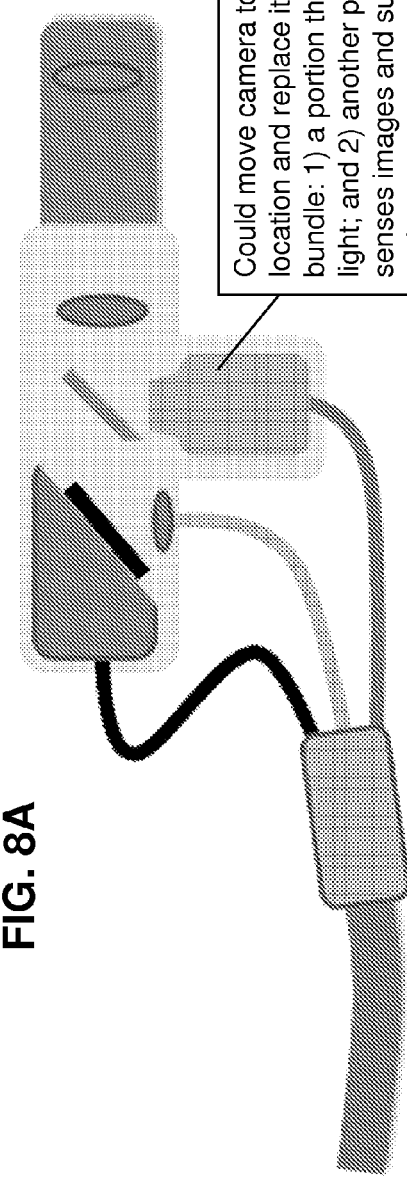
FIG. 8C
Could move camera to remote location and replace it with fiber bundle: 1) a portion that generates light; and 2) another portion that senses images and supplies them to the camera

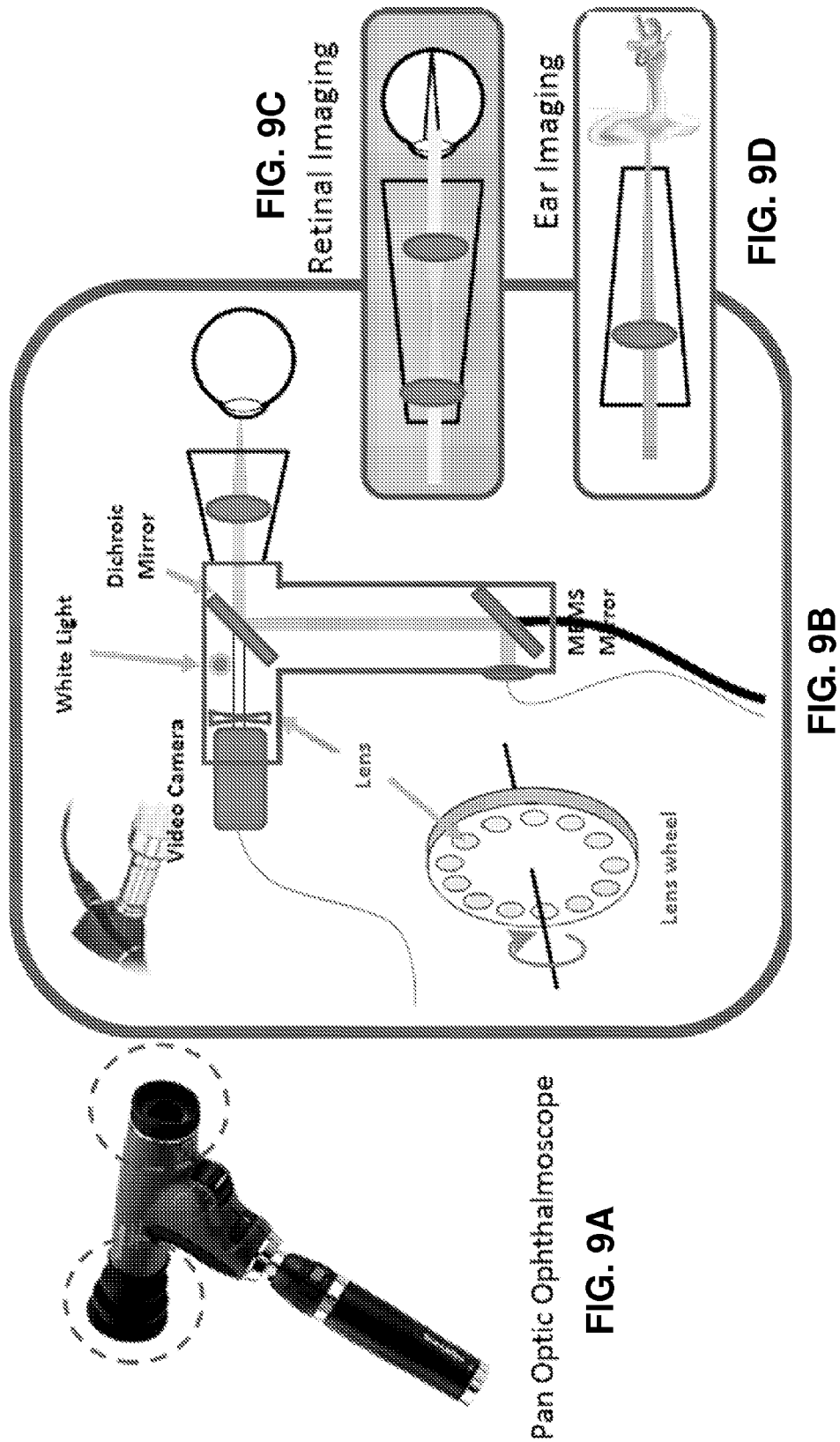

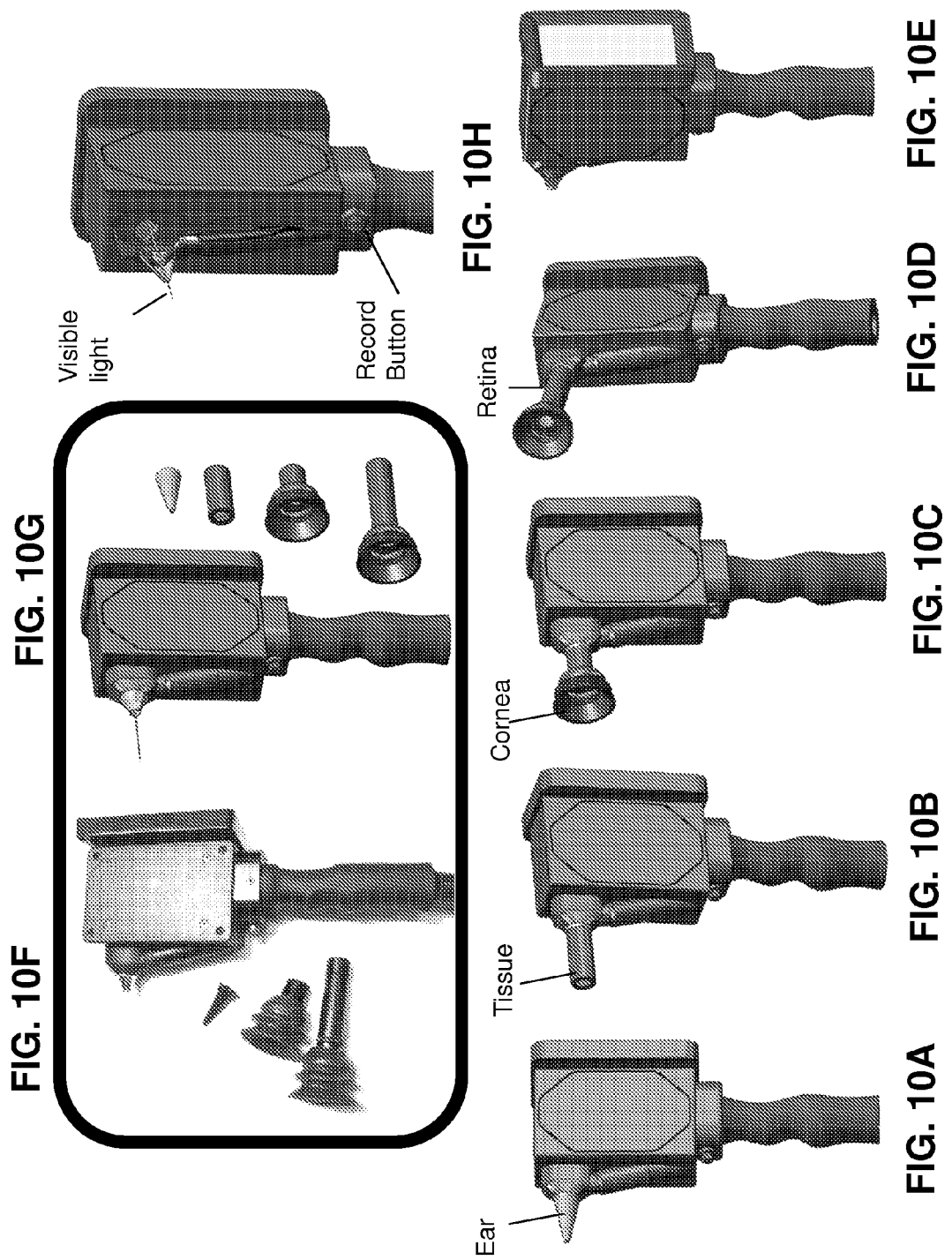

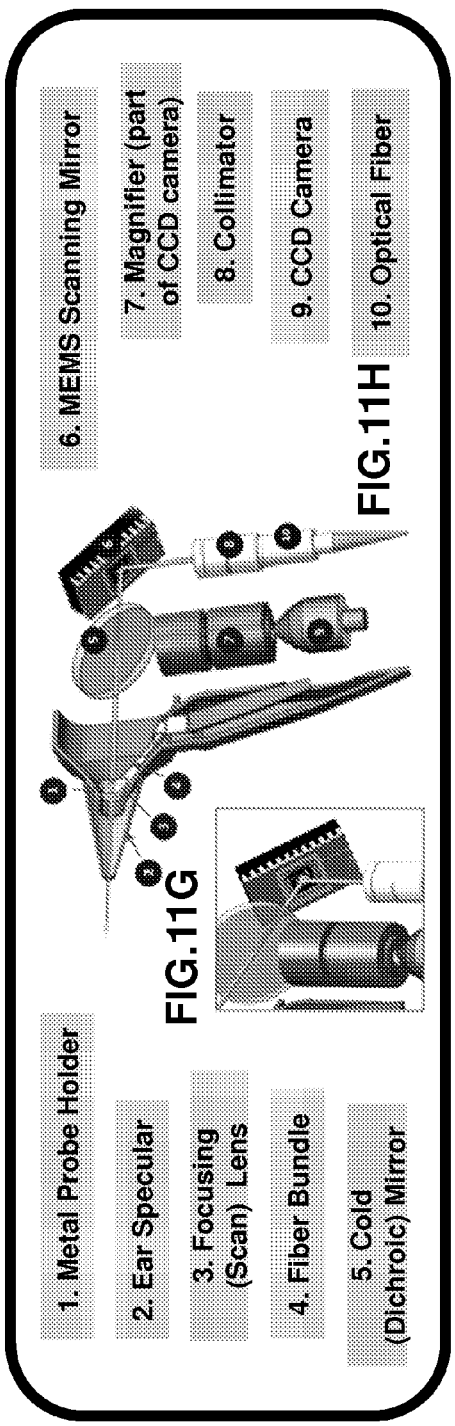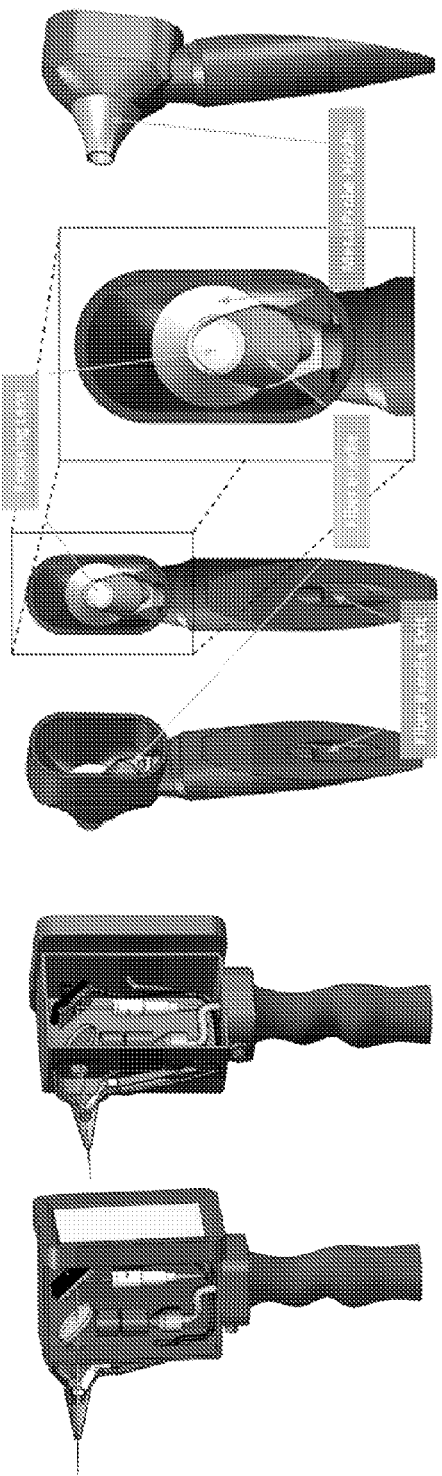

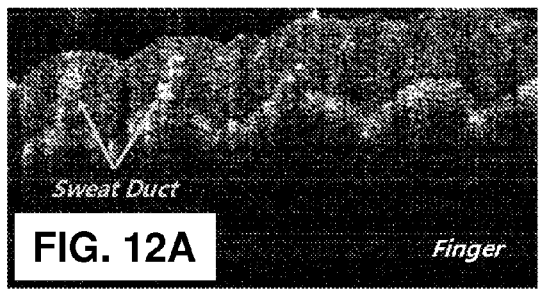
FIG. 12A
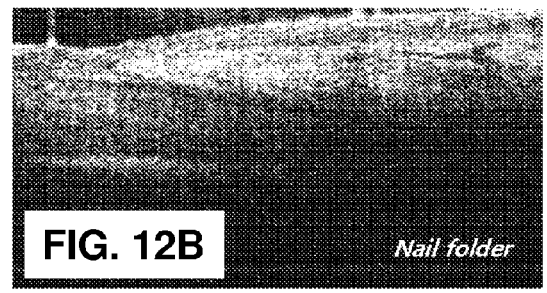
FIG. 12B
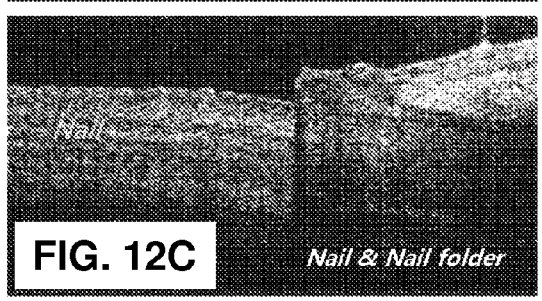
FIG. 12C
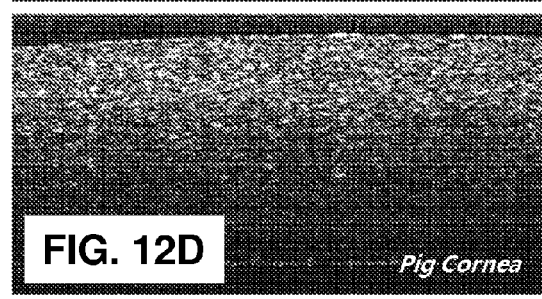
FIG. 12D
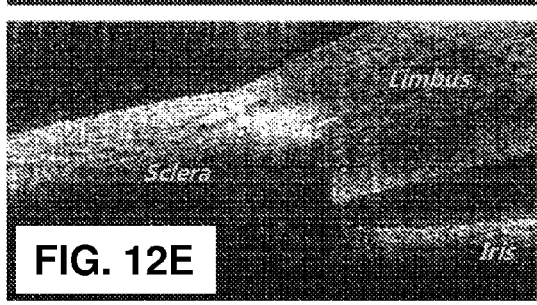
FIG. 12E
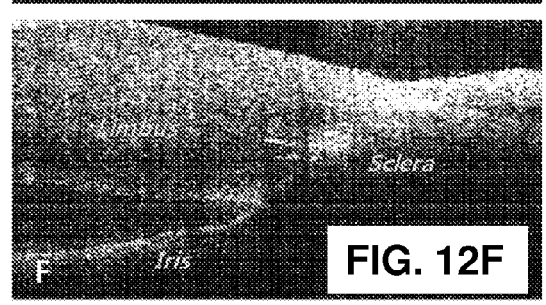
FIG. 12F

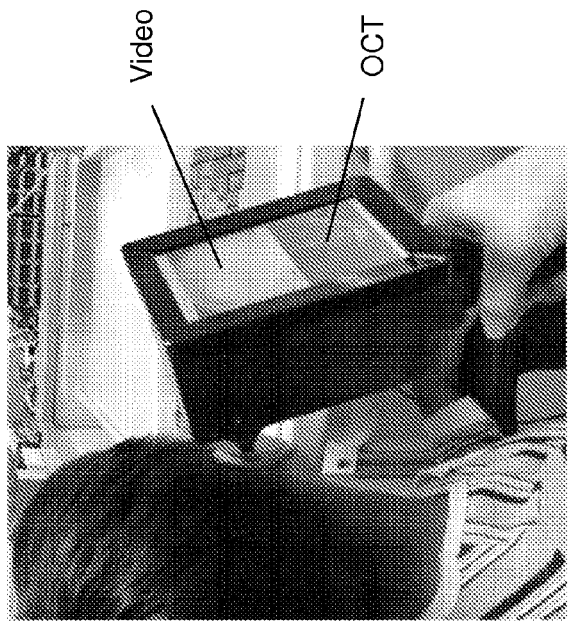
FIG.13H
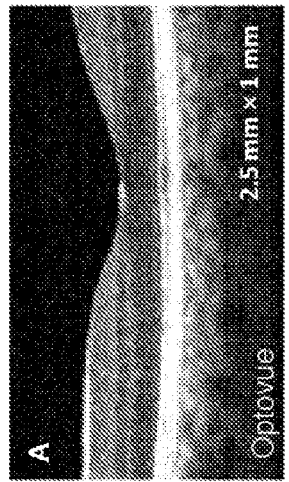
FIG.13A
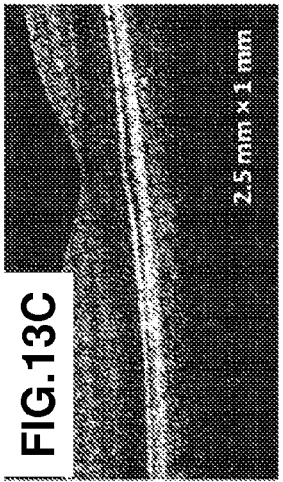
FIG.13B
FIG.13C
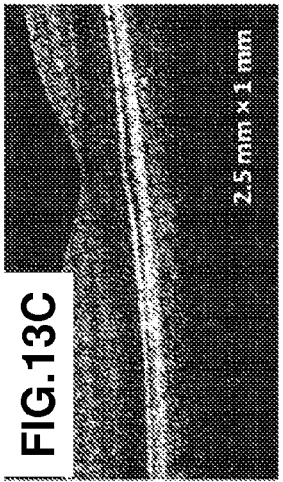
FIG.13D
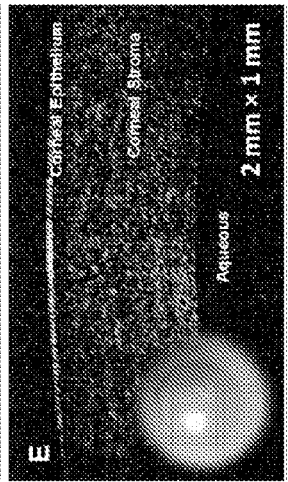
FIG.13G
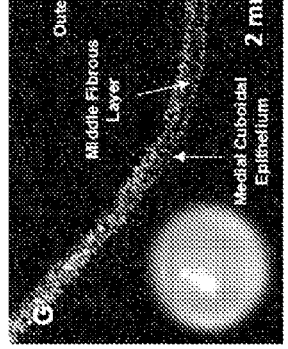
FIG.13E
FIG.13F

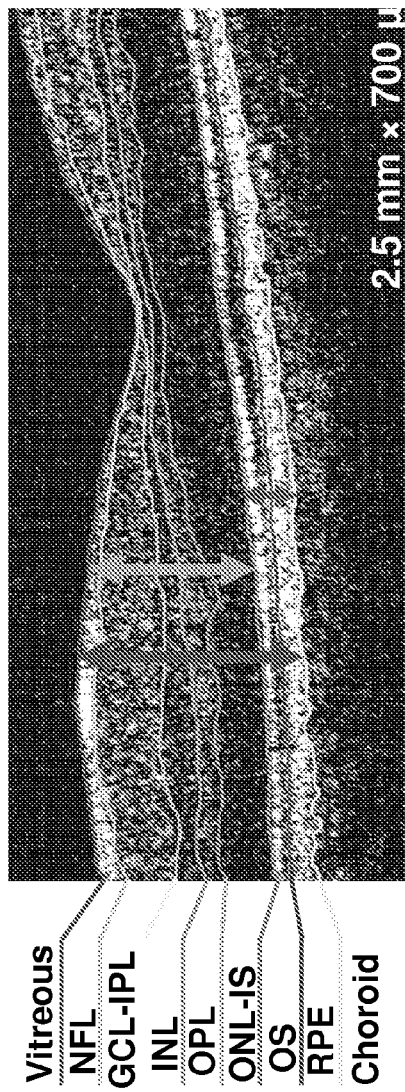
FIG.14B
Vitreous
NFL
GCL-IPL
INL
OPL
ONL-IS
OS
RPE
Choroid
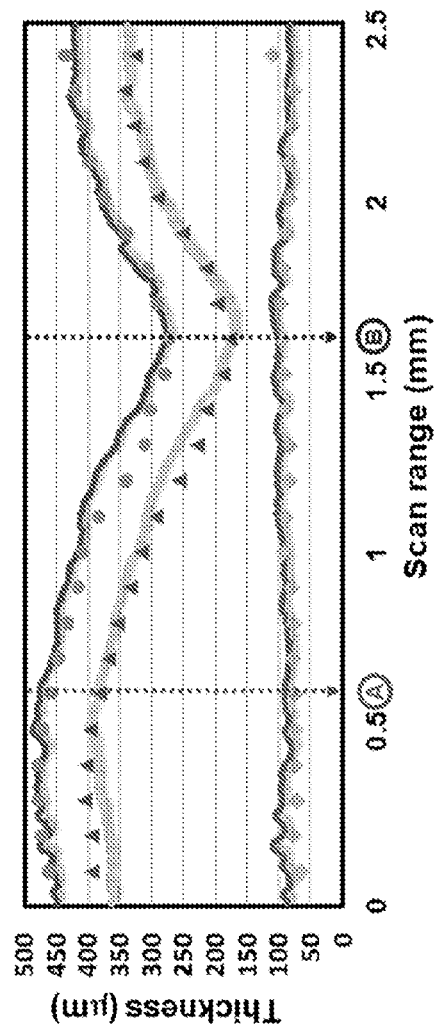
FIG.14A
*Solid line:*
*Manual segmentation*
*Dot line:*
*Automatic segmentation*

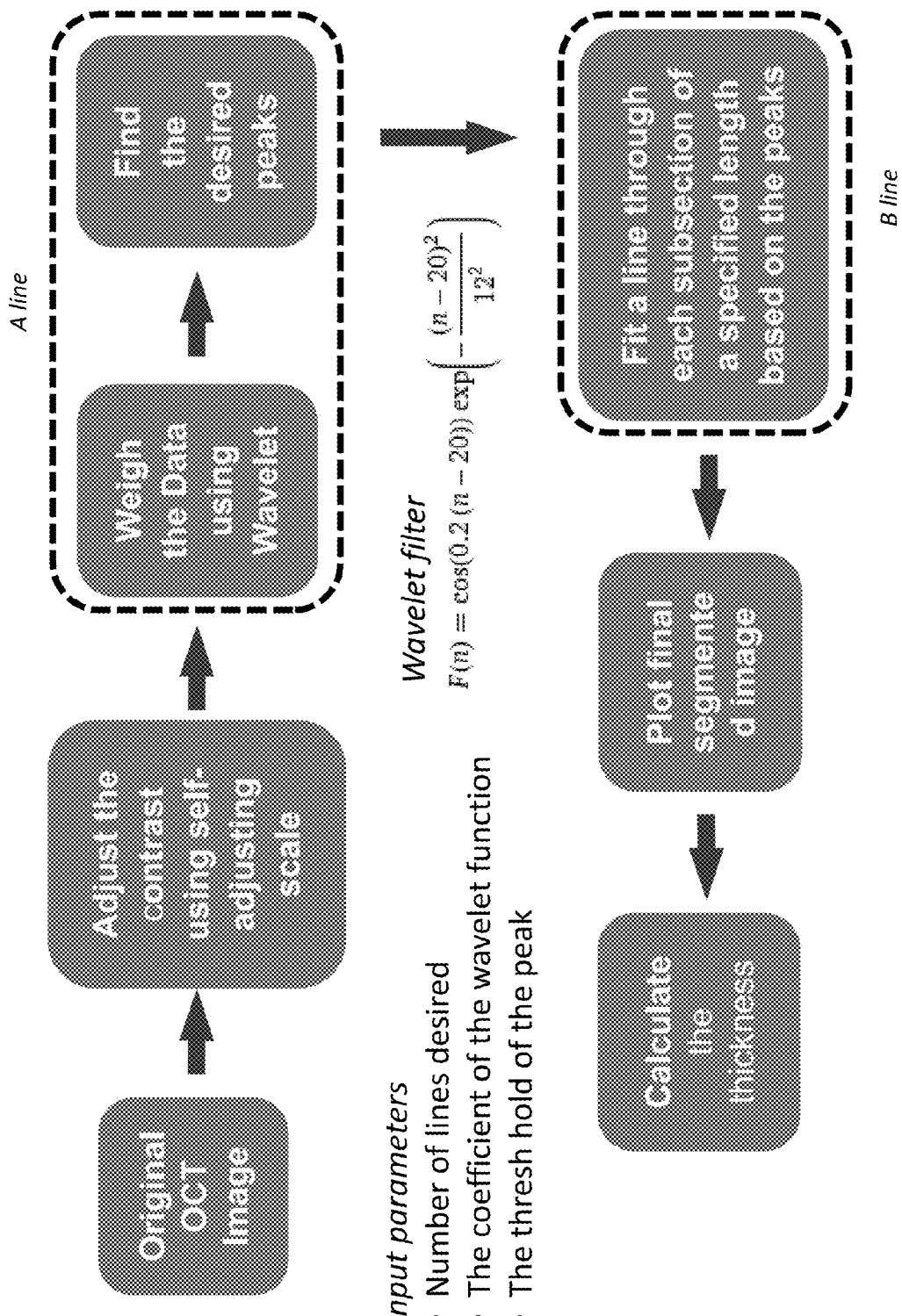
FIG.15

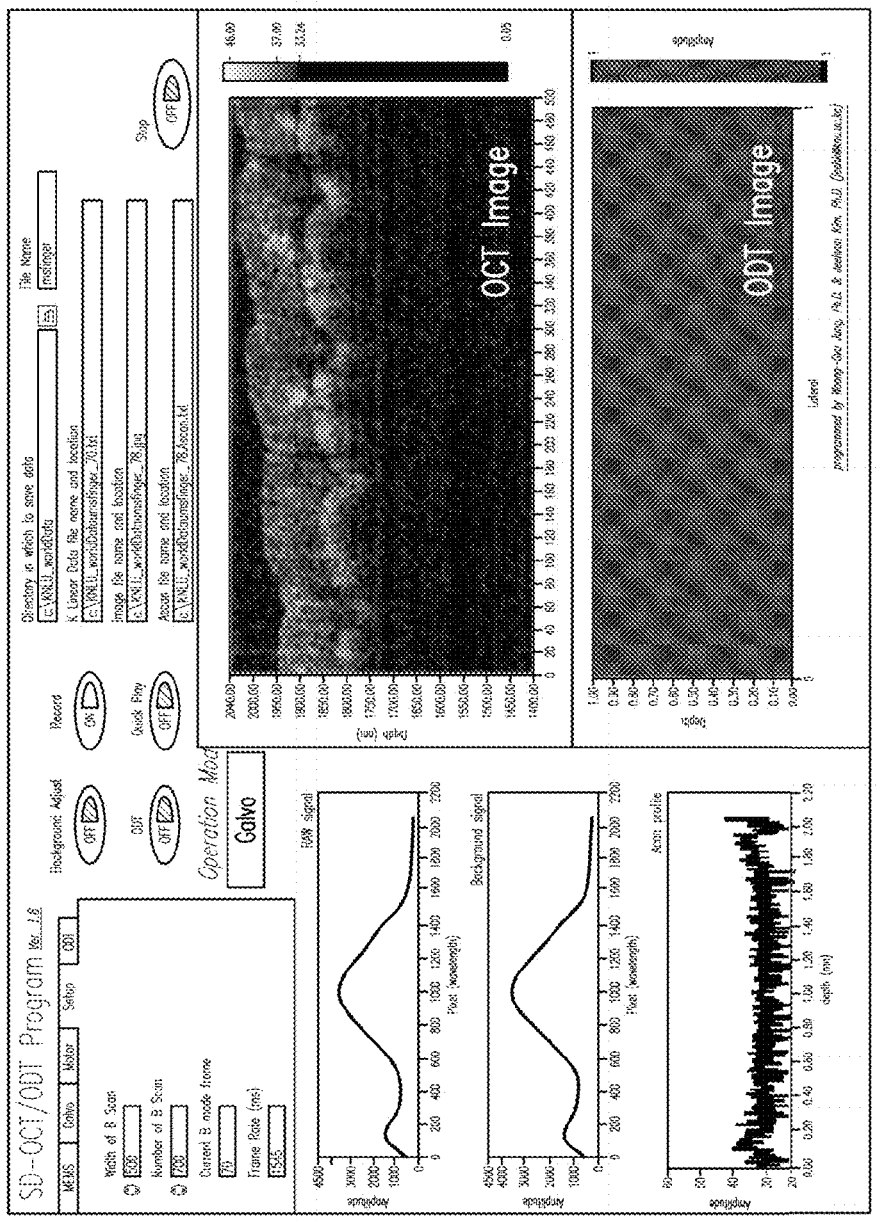
FIG. 16

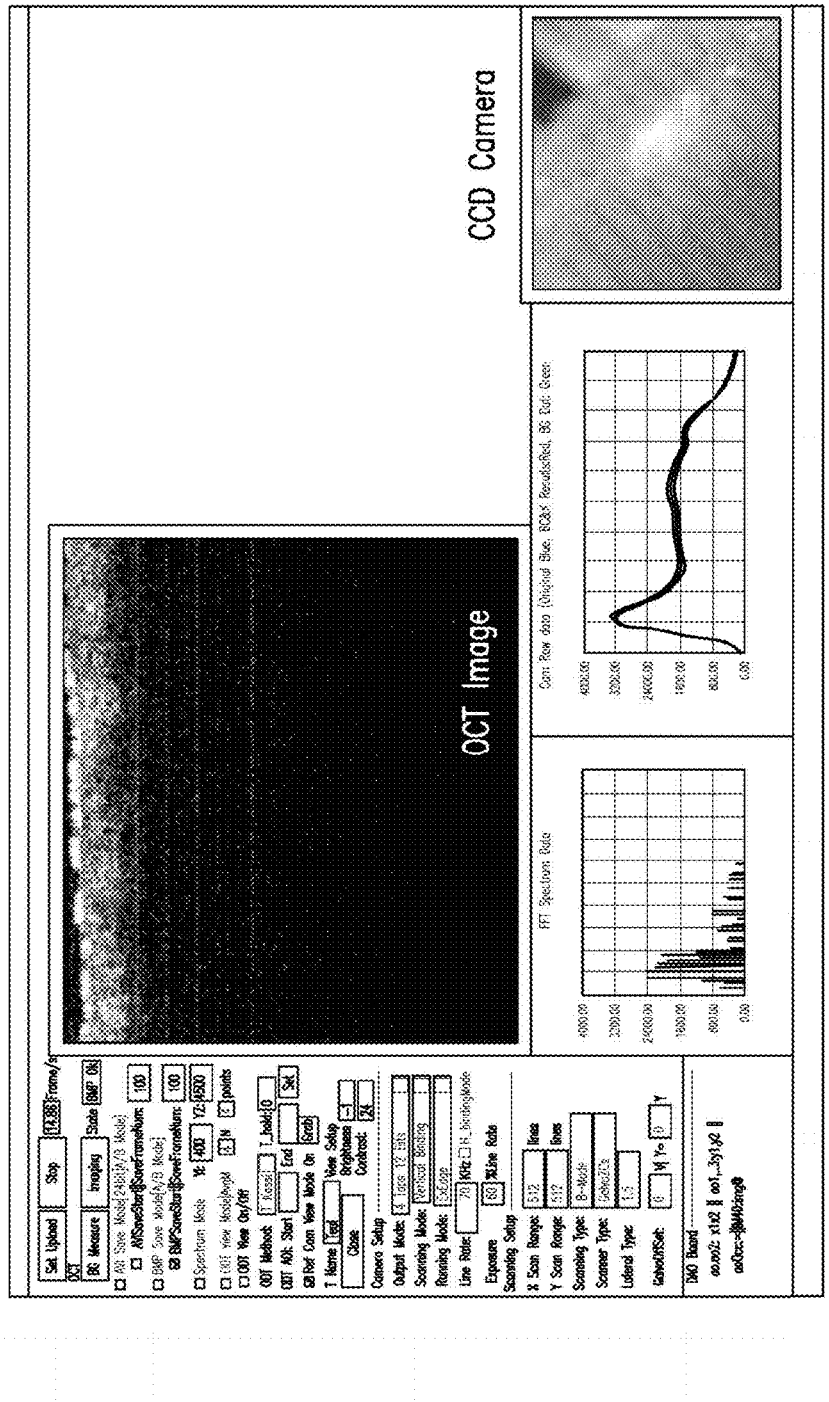
FIG. 17

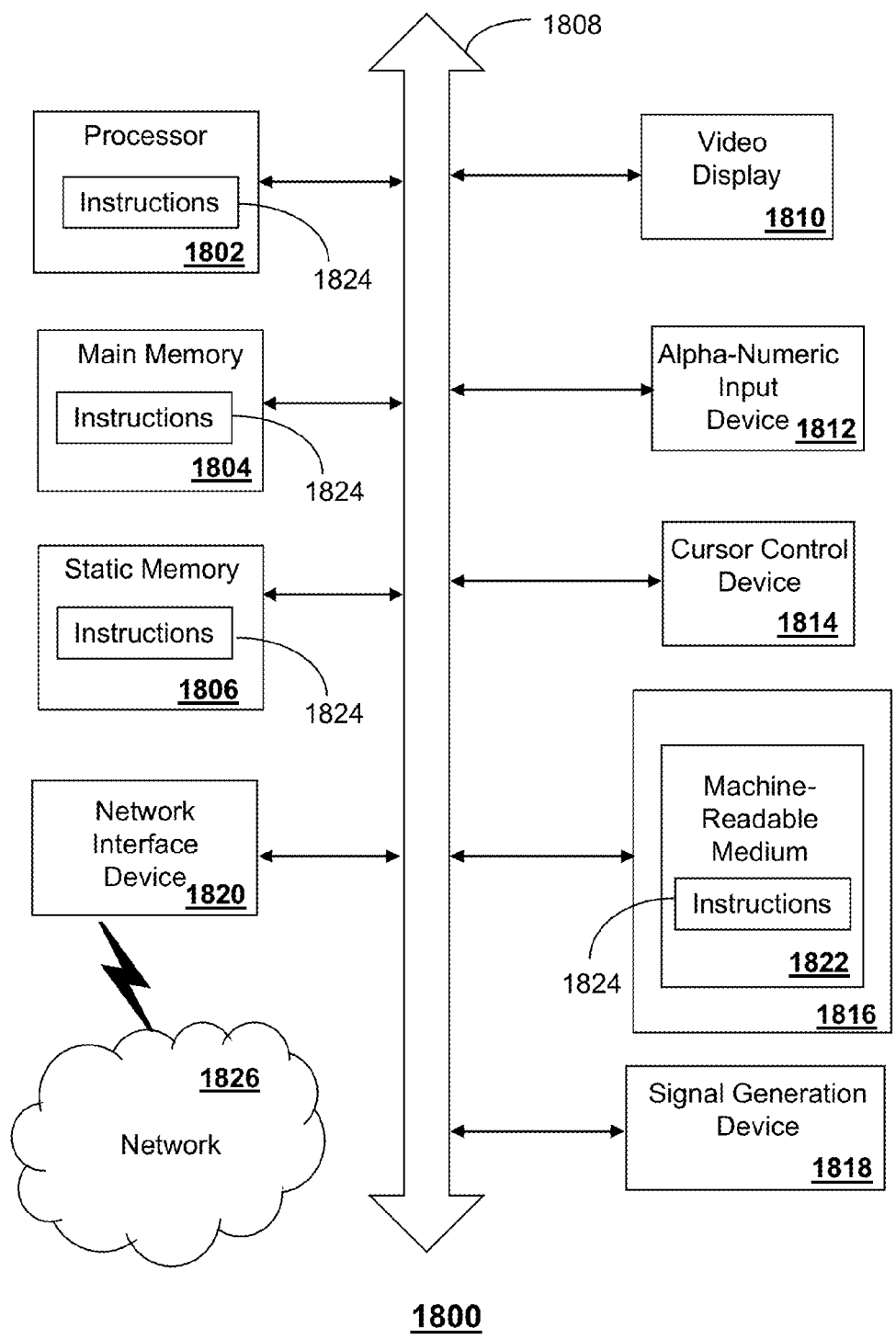
FIG. 18

| Hardware description | System performance |
|---|---|
| Source (Superlum)<br>Type: SLD<br>Center wavelength: 840 nm<br>FWHM: 70 nm<br>Optical power: more than 12 mW | Sensitivity<br>: more than 95 dB<br><br>10 dB roll-off depth<br>: 1.3 mm |
| Line CCD Camera (Basler)<br>Type : Dual line CMOS<br>Pixel per line: 2048<br>Pixel depth: selectable 8, 10, 12 bit<br>Max line rate: 140 kHz | Axial resolution (air)<br>: 7 μm<br><br>Lateral resolution<br>: 15 μm |
| MEMS scanner (Advanced MEMS)<br>Actuator type: Vertical comb driven electrostatic actuator<br>Scanning domain: 4 Quadrant<br>Size of actuator: 3.3 × 2.6 mm<br>Mirror size: 2.2 mm and 3.3 mm<br>Resonance frequency: 1kHz at each axes @ 2.2 mm<br>Scanning angle: 15° (optical) | Image size<br>: 2048 × 500 pixels<br><br>Image acquisition time<br>: 15 fr/s @ saving mode<br><br>Camera operating mode<br>: Free run or edge control |
| Grating: 1800lp/mm | |

FIG. 19

APPARATUS FOR BIOMEDICAL IMAGING

PRIOR APPLICATION

The present application claims the priority of U.S. provisional patent application No. 61/262,429 filed Nov. 18, 2009. All sections of the aforementioned application are incorporated herein by reference.

FIELD OF THE DISCLOSURE

The present disclosure relates generally to biomedical imaging devices, and more specifically to an apparatus for biomedical imaging.

BACKGROUND

Biomedical imaging combines many principles of electrical engineering, physics, medicine, and biology. One emerging biomedical imaging modality is optical coherence tomography (OCT). OCT is the optical analogue to ultrasound imaging, except near-infrared light is used, rather than sound, to generate high-resolution, cross-sectional optical images based on the intrinsic optical scattering properties of tissue. Because light is used, cellular-level resolution, on the order of 5-10 microns, is feasible, to imaging depths up to 3 mm in highly-scattering tissue such as skin, or completely through the eye, the retina, and into the choroidal (vascular) areas behind the retina. There are numerous applications for OCT in medicine and surgery, where it can be thought of as performing an "optical biopsy" of tissue, rather than having to physically resect tissue, process it, and section it for observation on microscope slides using a standard white-light microscope.

OCT has been demonstrated extensively in medical, surgical, and biological applications since its inception in 1991, offering unique imaging performance including non-contact, high resolution, and real-time imaging. Among several applications, ophthalmic imaging using OCT has been the most successful application. First, the eye provides a uniquely suitable medium for OCT due to its transparent nature, minimal scattering, and excellent light penetration compared to other biological tissues. Second, imaging of the eye has grown significantly in importance for the diagnosis of ocular diseases. However, there are few techniques available other than scanning laser polarimetry and confocal scanning laser ophthalmoscopy.

Third, OCT provides information showing cross-sectional structures of the cornea and retina that cannot be obtained by any other non-invasive diagnostic technique, enabling an enhanced understanding of the pathogenesis of disease and the response to therapy. These properties have made OCT a unique ophthalmic diagnostic modality, and a commercially available product. The first commercially available OCT, called OCT 1000 (Carl Zeiss Meditec, Inc), was marketed in 1996. A variety of commercial ophthalmic OCT systems have since developed. In 2006, the first high-speed, high-resolution OCT 3 (Carl Zeiss Meditec, Inc) became the "gold standard" for retinal imaging. Current commercial ophthalmic OCT systems and their performance specifications are summarized in FIG. 1.

BRIEF DESCRIPTION OF THE DRAWINGS

FIG. 1 depicts an illustrative embodiment of commercial ophthalmic optical coherence tomography (OCT) companies and its system specification;

FIGS. 2A-2B depict an illustrative embodiment of a commercial ophthalmoscope used by primary physicians and their staff;

FIG. 3 depicts an illustrative embodiment of a schematic of an OCT imaging apparatus;

FIGS. 4A-4C and 5A-5E depict illustrative embodiments of micro-electro-mechanical system (MEMS) scanning mirrors;

FIGS. 6A-6B depict illustrative embodiments of photographs of a sample arm (A) and DIP chip-mounted 2 axis MEMS scanner (B);

FIGS. 7A-7B depict illustrative embodiment of photographs of a portable prototype OCT system;

FIGS. 8A-8B, FIGS. 9A-9D, FIGS. 10A-10H and FIGS. 11A-11H depict illustrative embodiments for packaging portions of a sample arm of FIG. 3 into a handheld OCT probe;

FIGS. 12A-12F depict illustrative embodiments of OCT images of an in vivo human finger (A-C) and an in vitro anterior segment from a pig eye (D-F). Image (A) was acquired using the two-axis MEMS scanner and images (B-F) were acquired using a pair of galvanometer-mounted mirrors;

FIGS. 13A-13H depict illustrative embodiments of OCT images of a retina with a commercial OCT system (A-B), and OCT images of a retina (C-D), cornea (E), finger (F), and tympanic membrane (G) captured with the prototype system of the present disclosure;

FIGS. 14A-14B depict illustrative embodiments of OCT images of segmented retina layers captured with the prototype system of the present disclosure, which can be used to measure tissue thickness and diagnose health condition(s);

FIG. 15 depicts an illustrative embodiment of a flow diagram for segmenting the retina layers of FIG. 14 and measuring tissue thickness;

FIGS. 16-17 depict illustrative embodiments of software used for capturing OCT images;

FIG. 18 depicts an illustrative diagrammatic representation of a machine in the form of a computer system within which a set of instructions, when executed, may cause the machine to perform any one or more of the methodologies disclosed herein; and FIG. 19 depicts an illustrative embodiment of a configuration of components and system performance of a prototype operative according to the present disclosure.

DETAILED DESCRIPTION

One embodiment of the present disclosure describes a medical diagnostic device having an optical coherence tomography (OCT) imaging probe. The OCT imaging probe can have a collimator, a micro-electro-mechanical system (MEMS) scanning mirror that receives one or more wavelengths of light supplied through the collimator, an image sensor, a beam splitter for splitting light reflected from a body part of a patient into first and second portions, wherein the first portion of light is supplied to the image sensor, and wherein the second portion of light is supplied to the MEMS scanning mirror, and an interchangeable module operable for coupling to the OCT imaging probe for observing the body part of the patient.

One embodiment of the present disclosure entails a computer-readable storage medium having computer instructions to generate images from spectral data supplied by an OCT imaging probe having a collimator, a MEMS scanning mirror, and a partial reflector for supplying images to an image sensor.

One embodiment of the present disclosure entails a method involving capturing spectral interference from an OCT imaging probe comprising a MEMS scanning mirror, and a partial reflector for supplying images to an image sensor.

A prototype OCT ophthalmoscope system ("instrument") was developed, a description of which follows. A goal of the instrument was to provide portability as well as fast imaging for use in a primary care setting. The instrument was implemented with these considerations in mind. The entire system was designed and equipped in a medical cart which is able to contain and carry an optical setup, computer, monitor, control units, and other accessories. In order to provide easy access to a patient, an initial imaging handheld probe was designed with miniaturized components such as a micro-electro-mechanical system (MEMS) scanning mirror and compact charged coupled device (CCD) camera, and was built on a small optic alignment rail. The prototype instrument was adapted for visualization of different aspects of body tissue with an ability to resolve 2D/3D OCT images simultaneously.

In one embodiment, the prototype instrument was tested in vivo and in vitro to image a human finger and a pig eye, respectively. The OCT system took 1 second to acquire 15 frames of 2D OCT images (2048×500 pixels) which were saved with the video images from the CCD at the same time. The resolution of the OCT images were 7 µm (vertical) and 15 µm (lateral), which is comparable to the commercial desk-style ophthalmic OCT systems.

FIGS. 2A-2B depicts a conventional non-OCT ophthalmoscope with common mechanical and optical components utilized by primary physicians. FIG. 3 a schematic of a spectral domain (SD) OCT system contemplated by the present disclosure. As should be evident from the components shown in FIG. 3, there is almost no commonality between non-OCT probe of FIGS. 2A-2B and the SD-OCT system of FIG. 3.

The schematic diagram of the prototype SD-OCT system of FIG. 3 can be based on a fiber optic Michelson interferometer configuration. Two light sources, a super luminescent diode (SLD) source (Supelum) 302 including an isolator, and a visible light source 304, were used for imaging and monitoring, respectively, of tissue. Light from both sources can be combined by a 2×1 fiber coupler 306, guided into one port of a 2×2 fiber coupler 308, and split into reference and sample arms 310 and 312. The reflected signals from each arm are recombined at the 2×2 fiber coupler 308 and the resulting spectral interference is captured by a spectrometer 318. Spectral data from a camera (Basler) of the spectrometer are then digitized by a frame grabber (e.g., National instruments), sampled, and rescaled as a function of the wave number, and finally visualized with a display after image processing. The optical setup, except for the sample arm and the light sources, is contained on a 12"×18" optical alignment board to fit within a small portable medical cart.

Light in the sample arm 312 is directed to the patient's eye after reflecting off of a two-axis MEMS scanner (see illustrations of FIGS. 4A-5E) and passing through other optical components. The components of the sample arm 312 can be housed in a compact OCT handheld probe as will be described shortly. The sample arm 312 was designed for both anterior segment (scan lens only) and retinal imaging (scan lens plus ocular lens) by the removal or inclusion of the ocular lens which can be managed with an interchangeable module as will be discussed below. The setup is equipped for retinal imaging, but can easily be changed for anterior segment imaging by tilting a flip-mounted mirror and lens. In order to match dispersion, dispersion compensation units were also used in the reference arm 310. The entire imaging procedure can be monitored and recorded by a CCD camera (in the sample arm 312) which can be used by the operator to direct the OCT beam to the desired imaging site within the eye.

FIGS. 6A-6B depict illustrative embodiments of photographs of a sample arm (A) and DIP chip-mounted 2 axis MEMS scanner (B) used in an initial proof of concept of the SD-OCT prototype system.

The aforementioned two-axis MEMS scanner was used for 2D/3D imaging. The two-axis MEMS-based scanner has many advantages including rapid scanning, small size, high reliability, and flexibility in scanning pattern capabilities. In addition, a single two-axis MEMS scanner provides a compact size and simple operation compared to the conventional scanning mechanisms which employ successive single axis scanners with multiple axes, i.e., paired galvanometer scanners. Thus, the two-axis scanning MEMS mirror can be a desirable component to realize a portable and compact handheld ophthalmoscope, and also applicable for use in an advanced OCT-imaging otoscope.

Unlike conventional two-axis MEMS scanners, the prototype ST-OCT system of the present disclosure used a customized four-quadrant MEMS scanner. A typical one-quadrant device achieves mechanical tilt from 0° to a certain positive angle on each axis, while a four-quadrant device can operate from negative to positive angles on both axes. Under such conditions, a one-quadrant device addresses points only in the $1^{st}$ quadrant, while a four-quadrant device has scan capabilities in all four quadrants. Thus, this device gives a larger field of view in imaging applications and offers simplified alignment in the packaging without having to compensate and calibrate for offset problems at a 0° rest angle.

After initial testing of the OCT prototype system, all components and instruments separated from the sample arm were integrated into a portable medical cart (26" depth×20" width× 37" height) shown in FIGS. 7A-7B. The size of this prototype system is very compact and comparable to current commercial OCT systems, considering the capacity of the optics and other off-the-shelf instrument components. Recognizing that this initial prototype was constructed from off-the-shelf components and pre-packaged instruments, with good design engineering and systems integration, this unit can be reduced in size to 6"×12"×12", and can be wall-mounted.

FIGS. 8A-11H depict illustrative embodiments for packaging the sample arm 312 of FIG. 3 into a handheld OCT probe. FIGS. 8A-8C depict an embodiment for housing the collimator, two axis MEMS scanner, Dichroic mirror, CCD camera and scan lens in a handheld housing assembly. The ocular lens can be modular. FIGS. 9A-9D depicts another embodiment for housing the sample arm in a handheld probe. In this embodiment, a lens wheel much like the lens wheel used in conventional ophthalmoscopes can be employed in the OCT handheld probe for easily interchanging optical lenses during or before observing a patient.

FIGS. 10A-10H depicts an OCT handheld probe with interchangeable modules for observing a patient's ear, tissue, cornea, and retina (using ocular lens in the module). Other interchangeable modules suitable for the present disclosure are contemplated such as for modules for observing a throat cavity, nasal cavity, rectal cavity and so on. The handheld probe can also be equipped with a visible light source which exits the interchangeable module which can be used to aim at a tissue under observation. Additionally, the handheld probe can be equipped with a user interface such as a display and buttons. A record button shown in FIG. 10H can be depressed to signal an imaging system to begin recording OCT and video images until the record button is released (or depressed a second time—in the case of a toggle function). FIGS. 11A-11H depict how the sample arm components can be positioned in a handheld probe. The exemplary device can record one or more still or moving images from the spectral interference and images supplied to a camera: and can cause one or more audible alerts to indicate at least one of a start of recording of a still image, a start of recording of a moving image, an end of recording of a still image, and an end of recording of a moving image.

The software developed for this system was adapted to control the ophthalmic OCT system, which provided verification of its performance. The software developed was based on Labview and Visual C++, shown respectively, in FIGS. 16-17. The software portion in Labview incorporated test functions, signal processing units, different saving modes, and flexible hardware control. After testing the OCT system using Labview-based software, optimal parameters such as fast control and signal processing functions were identified and used to design a clinical version of the software. The resulting clinical version used Visual C++, which enabled fast image data acquisition and practical functionality. FIG. 19 presents both the measured system performance and the specifications of the hardware and software used in the OCT prototype system.

As a first evaluation of the imaging capabilities of the prototype system, a high speed imaging of an in vivo human finger and an in vitro anterior eye segment from a pig were performed. The image of FIG. 12(A) was acquired using the MEMS scanner, while the images of FIGS. 12(B-F) were acquired using a pair of galvanometer-mounted mirrors. The acquired images consist of a total of 2048 axial sampled points, but only a portion of the full 2048 points are shown in FIGS. 12A-12F (those corresponding to tissue structures). FIG. 12(A) is 3 mm×1.5 mm size, while the size of FIGS. 12(B-F) is 7 mm×1.5 mm with 700 A-scans (columns across the image). With fast-mode software used with the prototype OCT system, imaging acquisition time was 15 frames/second having 2048 axial points and 500 A-scans (columns) making up each B-mode image.

Compared to FIG. 12(A), FIGS. 12 (B,C) present better contrast and brightness. This is likely due to the MEMS scanner having a temporary protective glass that has loss near the 800 nm wavelength and results in less signal and sensitivity. This can be corrected by replacing the standard glass window with anti-reflection-coated glass to reduce the loss of the 800 nm light. Based on the in vivo skin images, the current imaging speed of the prototype OCT system is sufficiently fast to avoid motion artifacts. FIGS. 12(D-F), showing images of the in vitro pig eye, demonstrate that the entire thickness of the cornea, from the surface to the endothelium, which can be clearly visualized, as well as the limbus, sclera and iris.

FIGS. 13A-13H depict illustrative embodiments of OCT images of a retina with a commercial OCT system (A-B), and OCT images of a retina (C-D), cornea (E), finger (F), and tympanic membrane (G) captured with the prototype OCT system of the present disclosure. In an embodiment where the OCT probe has a display, video and OCT images can be segmented in the display while observing tissue of a patient— see FIGS. 13A-13H.

From the foregoing descriptions, it would be evident to an artisan with ordinary skill in the art that the aforementioned embodiments can be modified, reduced, or enhanced without departing from the scope and spirit of the claims described below. For example, the aforementioned embodiments can be applied to other parts of a human (or animal's) body for observation and diagnostic purposes. For instance, the prototype instrument discussed above can be utilized to observe body portions such as an ear cavity, a throat cavity, a nasal cavity, a rectal cavity, or general tissue portions of a patient. Additionally, the prototype instrument can be adapted so that a plurality of selectable modules can be attachable to the OCT imaging probe. In this embodiment, the OCT imaging probe is a generic OCT monitor which changes its function depending on the module installed by a clinician to perform a diagnosis on a body portion of a patient.

The above embodiments can further be adapted to measure blood flow in a portion of a patient (human or animal) utilizing a Doppler OCT technique. Birefringence using a Polarization-Sensitive-OCT (PS-OCT) can also be used to perform analysis on tissue. For example Doppler can be used to characterize retinal blood flow, while PS-OCT can be used to quantify the retinal nerve fiber-layer thickness (an assessment for early-stage glaucoma).

FIGS. 14A-14B depict illustrative embodiments of OCT images of segmented retina layers captured using automated software in the prototype system of the present disclosure, which can be used to measure tissue thickness, thereby enabling a clinician to diagnose health condition(s). FIG. 15 depicts an illustrative embodiment of a flow diagram for segmenting the retina layers of FIGS. 14A-14B and for measuring tissue thickness. The software used by the prototype OCT system can be adapted to perform tissue thickness analysis using the flow diagram of FIG. 15, which in turn can be used to detect health issues such as early-stage glaucoma noted earlier. Other health conditions such as diabetes may also be diagnosed by the aforementioned tissue thickness analysis.

FIG. 18 depicts an exemplary diagrammatic representation of a machine in the form of a computer system 1800 within which a set of instructions, when executed, may cause the machine to perform any one or more of the methods discussed above. In some embodiments, the machine operates as a standalone device. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a smart phone, a laptop computer, a desktop computer, a control system, a network router, switch or bridge, or any machine capable of executing a set of instructions (sequential or otherwise) that specify actions to be taken by that machine. It will be understood that a communication device of the present disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methods discussed herein.

The computer system 1800 may include a processor 1802 (e.g., a central processing unit (CPU), a graphics processing unit (GPU, or both), a main memory 1804 and a static memory 1806, which communicate with each other via a bus 1808. The computer system 1800 may further include a video display unit 1810 (e.g., a liquid crystal display (LCD), a flat panel, or a solid state display. The computer system 1800 may include an input device 1812 (e.g., a keyboard), a cursor control device 1814 (e.g., a mouse), a disk drive unit 1816, a signal generation device 1818 (e.g., a speaker or remote control) and a network interface device 1820.

The disk drive unit 1816 may include a non-transitory machine-readable medium 1822 on which is stored one or more sets of instructions (e.g., software 1824) embodying any one or more of the methods or functions described herein, including those methods illustrated above. The instructions 1824 may also reside, completely or at least partially, within the main memory 1804, the static memory 1806, and/or within the processor 1802 during execution thereof by the computer system 1800. The main memory 1804 and the processor 1802 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine readable medium containing instructions 1824, or that which receives and executes instructions 1824 from a propagated signal so that a device connected to a network environment 1826 can send or receive voice, video or data, and to communicate over a network 1826 using the instructions 1824. The instructions 1824 may further be transmitted or received over the network 1826 via the network interface device 1820.

While the machine-readable medium 1822 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methods of the present disclosure.

The term "machine-readable medium" shall accordingly be taken to include, but not be limited to: solid-state memories such as a memory card or other package that houses one or more read-only (non-volatile) memories, random access memories, or other re-writable (volatile) memories; and a magneto-optical or optical medium such as a disk or tape. Accordingly, the disclosure is considered to include any one or more of a machine-readable medium or a distribution medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are periodically superseded by faster or more efficient equivalents having essentially the same functions. Wireless standards for device detection (e.g., RFID), short-range communications (e.g., Bluetooth, WiFi, Zigbee), and long-range communications (e.g., WiMAX, GSM, CDMA) are contemplated for use by computer system 1800.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A medical diagnostic device, comprising:
   an optical coherence tomography (OCT) imaging probe, comprising:
   a collimator;
   a micro-electro-mechanical system (MEMS) scanning minor that receives one or more wavelengths of light supplied through the collimator;
   an image sensor;
   a beam splitter for splitting reflected light that is reflected from a body part of a patient into first and second portions of the reflected light, wherein the first portion of reflected light is supplied to the image sensor, and wherein the second portion of reflected light is supplied to the MEMS scanning mirror; and
   an interchangeable module operable for coupling to the OCT imaging probe for observing the body part of the patient.

2. The medical diagnostic device of claim 1, wherein the image sensor corresponds to a charged coupled device (CCD) camera, wherein the patient corresponds to a human or animal, and wherein the CCD camera includes a light sources that generates additional light that reflects from the body part of the patient.

3. The medical diagnostic device of claim 1, wherein the OCT imaging probe is a handheld device, and wherein the interchangeable module comprises one or more optical lenses.

4. The medical diagnostic device of claim 1, wherein the interchangeable module is one of a plurality of modules, each module having different structure for observing different body parts of the patient.

5. The medical diagnostic device of claim 1, wherein the interchangeable module is used for observing an eye of the patient, and wherein the interchangeable module comprises:
   an eye cup that couples to a facial region of the patient centered about the patient's eye;
   a wheel with a plurality of lenses for measuring light reflected from the eye at various focal points; and
   a light source for directing the patient to focus vision on the light source.

6. The medical diagnostic device of claim 1, wherein the interchangeable module is used for at least one of observing a nasal cavity of the patient, observing an ear cavity of the patient, observing a throat cavity of the patient, observing a rectum cavity, observing a human cavity and observing tissue.

7. The medical diagnostic device of claim 1, comprising a plurality of light sources coupled to the OCT imaging probe by way of a fiber optic cable, wherein one light source produces an aiming beam projected on the body part of the patient, and wherein another light source produces adjustable or broad spectrum of wavelengths of light that reflect at various tissue depths of the body part of the patient.

8. The medical diagnostic device of claim 7, comprising a spectrometer to capture spectral interference generated by reflected signals from the OCT imaging probe.

9. The medical diagnostic device of claim 8, comprising a controller to:
   process spectral data from the spectrometer by digitizing, sampling, and rescaling the spectral data as a function of wave number; and
   present an image according to the processed spectral data.

10. The medical diagnostic device of claim 9, wherein the image is one of a two or three dimensional image.

11. The medical diagnostic device of claim 1, wherein the OCT imaging probe enables the observing the body part of the patient without utilizing a spectrometer.

12. The medical diagnostic device of claim 1, wherein the OCT imaging probe enables one or more audible alerts to be emitted in association with the observing of the body part of the patient.

13. A non-transitory computer-readable storage medium, comprising computer instructions, wherein execution of the computer instructions causes a processor to perform operations comprising:
   receiving spectral data supplied by an optical coherence tomography (OCT) imaging probe comprising a collimator, a micro-electro-mechanical system (MEMS) scanning mirror, and a partial reflector for supplying a first portion of reflected light to an image sensor and a second portion of the reflected light to the MEMS scanning mirror; and
   generating images from the spectral data.

14. The storage medium of claim 13, wherein the operations further comprise:
   processing the spectral data by digitizing, sampling, and rescaling the spectral data as a function of wave number; and
   presenting an image according to the processed spectral data.

15. The non-transitory computer-readable storage medium of claim 13, wherein the spectral data is derived from spectral interference, and wherein the imaging sensor is a camera remotely situated from the OCT imaging probe.

16. The non-transitory computer-readable storage medium of claim 15, wherein the spectral interference is captured by a spectrometer, and wherein the OCT imaging probe is coupled to a plurality of fibers comprising:
   a first portion of fibers coupled to a light source for delivering a variable or fixed source of light to the partial reflector, wherein the partial reflector delivers at least a portion of said variable or fixed light to a body part of a patient; and
   a second portion of fibers coupled to the camera and a lens for sensing the images supplied by the partial reflector.

17. The non-transitory computer-readable storage medium of claim 16, wherein the operations further comprise:
   recording one or more still or moving images from the spectral interference and the images supplied to the camera; and
   causing one or more audible alerts to indicate at least one of a start of recording of a still image, a start of recording of a moving image, an end of recording of a still image, and an end of recording of a moving image.

18. The non-transitory computer-readable storage medium of claim 17, wherein the operations further comprise enabling the start of recording via an actuation by one of a button at the OCT imaging probe, a foot pedal button, or a speech command.

19. A method, comprising:
   providing light to an optical coherence tomography (OCT) imaging probe comprising a micro-electro-mechanical system (MEMS) scanning mirror and a partial reflector for supplying a first portion of reflected light to an image sensor for capturing images and for supplying a second portion of the reflected light to the MEMS scanning mirror; and
   capturing spectral interference from the OCT imaging probe.

20. The method of claim 19, comprising generating images from the spectral interference.

21. The method of claim 19, comprising measuring blood flow in a portion of a patient with the OCT imaging probe.

22. The method of claim 21, comprising utilizing a Doppler OCT processing technique to measure the blood flow.

23. The method of claim 19, comprising analyzing tissue of a patient with the OCT imaging probe.

24. The method of claim 23, comprising utilizing at least one of a birefringence processing technique and a Polarization-Sensitive-OCT processing technique to analyze the tissue.

25. The method of claim 19, comprising presenting by way of a display on the OCT imaging probe at least one of a video image representative of an object under observation, and an OCT image of at least a portion of the object.

26. The method of claim 19, wherein the OCT imaging probe enables observing one of a human, animal or biological sample in association with the capturing of the spectral interference without utilizing a spectrometer.

27. The method of claim 19, further comprising providing audible alerts in association with the providing of the light.

* * * * *